United States Patent [19]

Gott, Jr. et al.

[11] Patent Number: 4,823,809
[45] Date of Patent: Apr. 25, 1989

[54] PERIODONTAL PROBE SYSTEM

[75] Inventors: F. Kenneth Gott, Jr., La Jolla; John T. Rickard; Stephen F. Connelly, both of San Diego, all of Calif.

[73] Assignee: Orincon Corporation, San Diego, Calif.

[21] Appl. No.: 88,152

[22] Filed: Aug. 21, 1987

[51] Int. Cl.$^4$ ............................................. A61B 5/10
[52] U.S. Cl. ................................... 128/776; 33/514
[58] Field of Search ............... 128/774, 776–777, 128/782; 33/511–514, 125 A, DIG. 3; 433/72

[56] References Cited

U.S. PATENT DOCUMENTS

| | | | |
|---|---|---|---|
| 3,058,225 | 10/1962 | Ward | 128/776 X |
| 3,916,529 | 11/1975 | Mousseau . | |
| 3,943,914 | 3/1976 | Grenfell et al. | 33/514 X |
| 4,250,895 | 2/1981 | Lees | 33/514 X |
| 4,275,505 | 6/1981 | Delmas | 33/DIG. 3 X |
| 4,340,069 | 7/1982 | Yeaple | 128/776 |
| 4,353,693 | 10/1982 | Dery et al. | 128/776 X |
| 4,364,730 | 12/1982 | Axelsson . | |
| 4,501,555 | 2/1985 | Ditchburn . | |
| 4,526,179 | 7/1985 | Salesky | 128/776 |
| 4,677,756 | 7/1987 | Simon et al. | 128/776 X |

FOREIGN PATENT DOCUMENTS

| | | | |
|---|---|---|---|
| 0061218 | 9/1982 | European Pat. Off. | 128/774 |
| 2022475 | 12/1979 | United Kingdom | 128/774 |

OTHER PUBLICATIONS

E. Sild, M. D., et al., "Computerized Periodontal Probe With Adjustable Pressure," The International Journal of Periodontics and Restorative Dentistry, 4/1987, pp. 52–62.
Vine Valley Research, "Specification For Model 200 Electronic Periodontal Probe," undated, (unnumbered) in total.
Robert J. Ryan, DDA, "The Accuracy of Clinical Parameters In Detecting Periodontal Disease Acitivity," JADA, vol. 111, Nov., 1985, pp. 753–760.

Primary Examiner—Max Hindenburg
Assistant Examiner—Angela D. Sykes
Attorney, Agent, or Firm—Baker, Maxham, Jester & Meador

[57] ABSTRACT

A periodontal probe system for measurement, storage, and display of periodontal pocket depth, gingival level and periodontal attachment level of the teeth. In the system, a periodontal probe instrument includes an elongate tip with a measurement arrangement that simultaneously measures periodontal pocket depth, gingival level, and periodontal attachment level at each of a plurality of probe sites around a tooth. The measurement arrangement provides depth signals indicative of the pocket depth and attachment level measured. Gingival level is computed as the arithmetic difference between the attachment level and the pocket depth. A pressure sensor in the probe provides a pressure signal indicative of the pressure acting on the tip of the probe. A signal processing apparatus is connected to receive the pressure signal and the depth signals. A periodontal measurement is made by inserting the tip of the probe into the gum pocket and gradually increasing the pressure on the probe tip after insertion. At a predetermined pressure level, the signal processing apparatus samples the depth signals and converts them into measurement signals corresponding to pocket depth and attachment level.

20 Claims, 7 Drawing Sheets

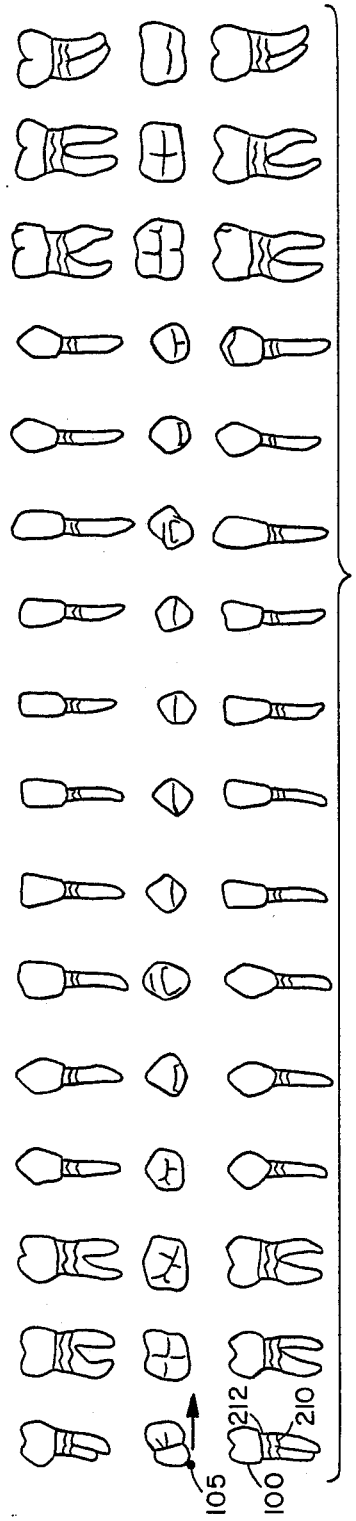
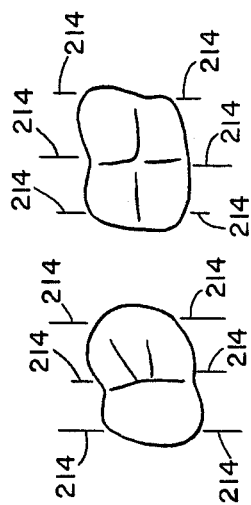
FIG. 10A
FIG. 10C
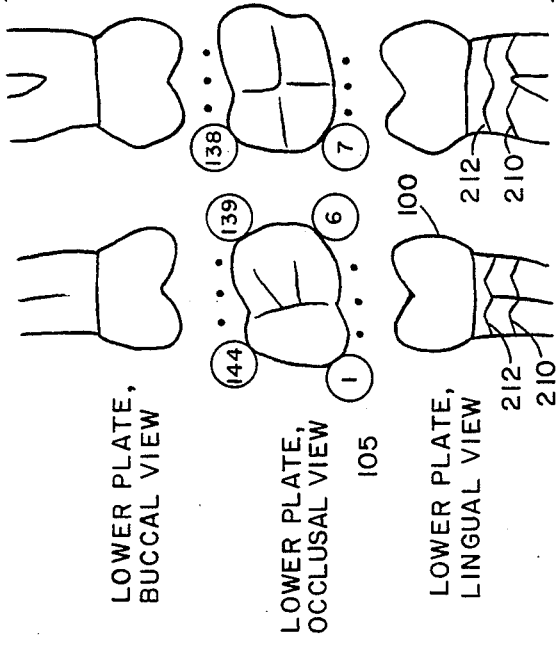
FIG. 10B

PERIODONTAL PROBE SYSTEM

BACKGROUND OF THE INVENTION

The invention is in the field of dental instruments, and particularly pertains to instruments for automatically making and recording periodontal pocket depth and attachment level measurements.

In the article entitled "The Accuracy of Clinical Parameters in Detecting Periodontal Disease Activity," by R. J. Ryan, Vol. III, *J.A.D.A.*, November 1985, the vital importance of periodontal probing measurements in the early detection and diagnosis of periodontal disease is clearly laid out. Of particular importance are the measurements of gingival ("gum") pocket depths and periodontal attachment levels. In this regard, a periodontal pocket is a recess formed between a tooth and adjacent gum tissue or bone as a result of disease activity such as periodontitis. The depth of the pocket is indicative of the progress and severity of the disease process. The periodontal attachment level is the distance from the incisal or occlusal edge of the crown or the cemento enamel junction of the tooth to the depth of the periodontal pocket. The gingival level is the distance from the edge of the crown or the cemento enamel junction to the top of the gum margin. As is known, periodontal disease activity can cause loss of the anchoring jaw bone. The progress of periodontitis can be determined by measuring attachment levels from which assessment of periodontal bone loss can be determined.

Typically, dynamic disease activity can be determined by accumulating, over time, a set of measurements of pocket depths, gingival levels, and attachment levels and comparing them with corresponding currently-measured depths. In fact, periodic measurements are recommended in order to provide early detection of periodontal disease and to track its progress, once detected.

It is vital that each set of measurements include measurements of both pocket depth and periodontal attachment level. If only periodontal pocket depth is measured and recorded, the extent and level of periodontal bone destruction and disease activity may be missed.

Traditionally, depth and level measurements have been taken manually, with a periodontal practitioner obtaining them visually from a probe tip with calibrated markings.

U.S. Pat No. 3,058,225 of Ward illustrates an instrument for automatically obtaining a measurement of attachment level by means of a probe with a fixed sheath which engages the crown of a tooth when a measurement is made. A slidable needle is moved through the sheath into the periodontal pocket, and the distance between the tip of the needle and the end of the sheath is essentially the periodontal attachment level. In U.S. Pat. No. 3,943,914 of Grenfell et al, a periodontal probe with a stationary needle measures pocket depth by a sheath which slides on the needle to the edge of the gingival margin of the pocket when the needle's tip engages the bottom of the pocket. The distance between the end of the sheath and the tip of the needle is converted into an indication of the depth of the periodontal pocket. Neither of these references provides guidance for determining both the periodontal pocket depth and periodontal attachment level simultaneously in a single measurement.

When considering the construction of a historical record comprising a series of periodically-made periodontal measurements, the Grenfell patent provides a system for converting the gingival pocket depth measurements into printed numerical representations. In this system, archiving evidently consists of accumulating and storing printed representations made at different times. It is assumed that these measurements are manually transcribed onto a dental chart. The detection of change in measurements, which is the best indication of disease activity, thus depends upon visual interpretation of the printed measurement record, and manual transcription of the results into chart form.

The need, summarized in the cited Ryan article, for periodic measurement of both pocket depth and attachment level in a form which accommodates the differential comparison of sets of periodically-obtained measurements is therefore not adequately met by any system known to the Applicants.

SUMMARY OF THE INVENTION

The invention is founded on a first critical observation that illumination of a patient's mouth during dental examination by a high-intensity dental lamp affords an opportunity to obtain the depth and level measurements of interest in a single measurement maneuver using optical technology. In this regard, a linear array of elements responsive to illumination is provided on a periodontal probe tip which is inserted into a gum pocket for measurement. Pocket depth is directly obtainable from the portion of the array shadowed by the pocket. In addition, attachment level is obtained by positioning an optical shield over the array at the crown of the tooth being measured. Gingival level is then computed as the arithmetic difference between the attachment level and pocket depth measurements. It is worth noting that current attachment level measurements done manually with the human eye have an error of ±1 mm. However, with the optical technology, employed according to the invention, measurements of ±0.1 mm will be realistic.

The second critical observation concerns the use of automated processing means having a storage capability to store a plurality of periodontal examination results for a single patient, thereby providing a capability of archiving periodontal measurement data useful for spotting the onset and tracing the progress of periodontal disease. Further, the processing means is capable of, and in the invention is employed to process the historical data and provide a presentation of change. This completely eliminates the requirement for hand transcription of periodontal measurement data onto dental charts, and eliminates the need for manual determination and rendering of measurement changes.

The invention, in one aspect, is a system for performing periodontal pocket depth, attachment level and gingival level measurements that includes a probe with an end and a handle surface, an electrical signal conductor in the probe, and a pressure sensor in the probe handle which is connected to provide a pressure signal on the electrical signal conductor indicative of a pressure acting on the probe tip. An elongate semiflexible tip is placed in the end of the probe. On the tip there is disposed a measurement arrangement which simultaneously measures periodontal pocket depth and periodontal attachment level and provides first and second depth signals on the electrical signal conductor indicative of the measurement of periodontal pocket depth and periodontal attachment level. A signal processing apparatus is connected to the electrical signal conductor and responds to pressure signals produced by the pressure sensor by receiving and converting first and second depth signals into measurement signals, by accumulating a set of measurement signals, and by storing an accumulated set of measurement signals in an examination file format. Finally, the system includes a display apparatus which responds to converted first and second depth signals by visibly displaying pocket depth, gingival level, and attachment level in a dental chart format.

The measurement arrangement on the elongate tip accomplishes the simultaneous measurement of periodontal pocket depth, gingival level, and periodontal attachment level by an array of opto-electronic elements which indicate light-to-dark transitions corresponding to the top of the gum pocket and the incisal or occlusal edge of the crown of the tooth. Relatedly, the measurement arrangement includes an array of opto-electrical elements disposed on the elongate tip and an optical shield slidably disposed on the tip over the array. The array includes an elongate strip of serially-connected charge-coupled device (CCD) cells longitudinally disposed on the tip. The optical shield includes an annular collar encircling the tip, a member radially attached to the collar for engaging the tooth crown, and a spring attached to and acting between the probe tip and the collar.

For the detection and analysis of change in periodontal pocket depth, attachment level, and gingival level measurements, the signal processing apparatus includes a differential process modality that compares an accumulated file of measurement signals with a previously stored file of measurement signals and produces a set of differential measurement signals representative of changes in pocket depths, gingival levels, and attachment levels based on the comparison. The display apparatus responds to the set of differential measurement signals by displaying changes over time in pocket depth, gingival level, and attachment depth in the dental chart format.

From another aspect, the invention embraces a method for making periodontal measurements with a periodontal probe apparatus that includes a probe, a tip in the probe, an illumination detector mounted externally on the probe tip, and a sensor which measures the force applied on the probe tip through the probe. The method of the invention includes the steps of iluminating the interior of the patient's mouth, inserting the tip into a periodontal pocket adjacent a tooth in the illuminated mouth and exerting a force on the tip via the probe while the tip is in the dental pocket. Last, when the force reaches a predetermined level, illumination transitions along the tip are detected and converted into respective periodontal pocket depth, gingival level, and attachment level measurements.

From still another aspect, the invention extends to a periodontal measurement system that includes a probe with a tip and a handle, means in the probe for indicating the magnitude of force applied between the probe end and probe handle, and an elongate tip in the probe end. Measurement means are provided on an external surface of the probe tip for obtaining simultaneous optical indications of pocket depth and attachment level in a single measurement maneuver and for providing first and second depth signals indicative of the measurements. This aspect of the invention further has means responsive to the indication of a predetermined force level for converting first and second depth signals into corresponding first and second measurement signals. First processing means accumulate a set of first and second measurement signals resulting from a plurality of measurements. Second processing means store an accumulated set of measurement signals in a predetermined examination record format. Third processing means provide a signal indicative of a predetermined sequence of probe sites. Last, display means display converted first and second depth signals in a dental chart format and further display the sequence of probe sites in the dental chart format while displaying first and second depth signals.

It is therefore a primary objective of the present invention to provide a system which simultaneously measures periodontal pocket depth, gingival level, and attachment level by means of a periodontal probe having a measuring arrangement on it with provision for performing the simultaneous measurements when the probe is inserted into a gum pocket.

An additional objective of this invention is to provide a system for automatically recording and electronically storing an accumulated set of periodontal measurements made with such a probe, while simultaneously displaying the location of the next probe site and the results of already-performed probe measurements.

A significant characteristic of this invention is the provision of an optical arrangement on the tip of a periodontal probe which uses ambient illumination to simultaneously measure periodontal pocket depth, gingival level and periodontal attachment level.

One distinct advantage of this invention is that, in a single measurement maneuver, periodontal pocket depth, gingival level and periodontal attachment level are measured.

A second significant advantage of the present invention is the automation of probe measurement record-keeping and presentation, thus eliminating the need for manual transcription of probe measurement data.

Other objectives, features, and advantages of this invention will become evident when the description following is read while reference is made to the below-described drawings.

BRIEF DESCRIPTION OF THE DRAWINGS

FIGS. 10A, 10B and 10C illustrate the dental chart format employed for display purposes in the present invention.

DETAILED DESCRIPTION OF THE PREFERRED EMBODIMENT

Figure 1:
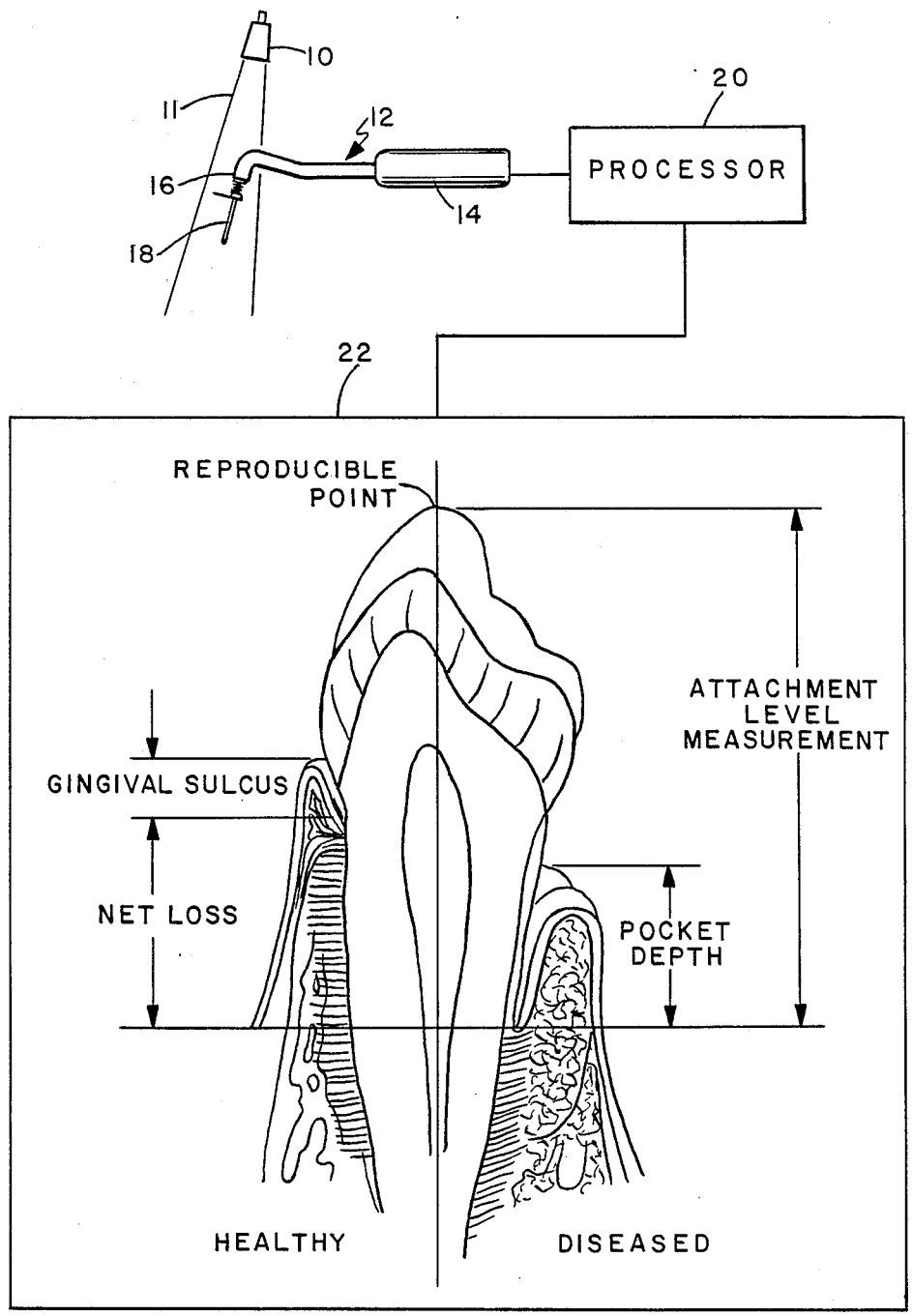
FIG. 1 illustrates the general arrangement of the invention in its intended operational environment.

Referring now to FIG. 1, the invention is intended to be most usually practiced within the environment of a dental office where an examination site is equipped with a high-intensity, overhead lamp 10 for providing illumination 11 of the mouth of a patient (not shown) being examined. Periodontal examination according to the invention is accomplished by a system including a periodontal probe 12 having a gripping handle 14 and a probe end 16 into which is inserted a probe tip 18. The periodontal probe 12 is handled in the conventional manner, with a periodontal specialist or technician taking measurements by inserting the probe tip 18 into a gum pocket and applying pressure to move the distal end of the tip 18 against the lower epithelial lining, against which measurement is made. Pressure on the tip 18 is applied by hand on the gripping surface 14. The system of the invention also comprises a processor 20 and a display 22. It is contemplated that the processor 20 can include any of a variety of commercially-available portable computers known generically as personal computers, or any equivalent thereof, such as, but not limited to, microcomputers, minicomputers, lap-top computers, or any other processor suitable for processing interconnection with a periodontal probe. Further, the processor 20 is understood to embody the capability of driving the display 22, which may, in fact, be integrated into a unitary frame with the processor 20.

In the practice of the invention, the illumination 11 from the lamp 10 provides energy for taking periodontal measurements by opto-electronic means, which convert the measurements from light signals to electrical signals, the electrical signals being provided through the periodontal probe instrument 12 to the processor 20 for processing described below.

In FIG. 1, the tooth illustrated on the display 20 is not the display provided by the invention, which is illustrated and described below. The tooth in FIG. 1 is intended to establish, with FIG. 2, the dental terms used in conjunction with the operation of the invention. Thus, the gingival sulcus is a furrow between the top of gum (gingival) tissue and an adjacent tooth. In healthy gums, this furrow is shallow, and bottoms where healthy gum tissue attaches to the tooth. In diseased gum tissue, the furrow deepens and becomes a pocket whose depth indicates the progress and severity of disease. As periodontal disease progresses, the level where the gum attaches to the tooth drops. Recession of the attachment level offers direct evidence of disease-caused bone loss where the tooth is anchored in the jaw. The two primary measurements of interest in analyzing periodontal pathology are periodontal pocket depth—the depth of the gum pocket adjacent the tooth—and periodontal attachment level—the level at which the gum attaches to the tooth. Both measurements are necessary. Bone loss may cause the attachment level to drop, while the pocket depth is unchanged. Measurement of only the pocket depth would not indicate disease activity in this case. Gingival level—the difference between the attachment level and pocket depth—is a derived measurement that is also commonly used in practice.

Figure 2:
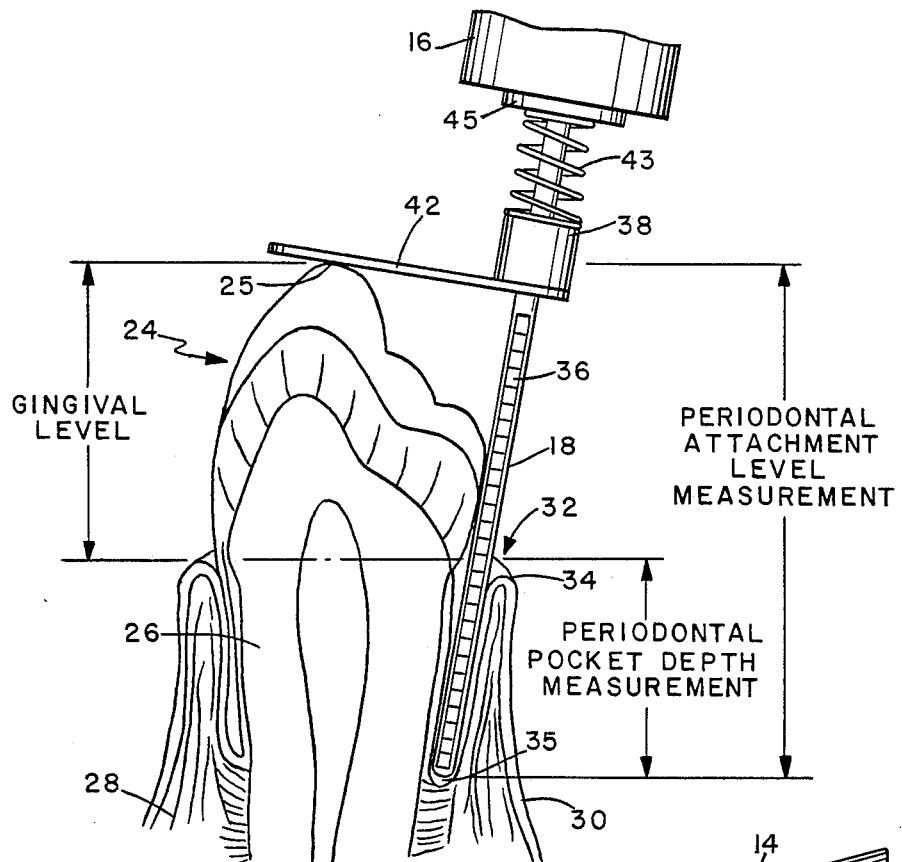
FIG. 2 illustrates how periodontal pocket depth, gingival level, and periodontal attachment level are simultaneously measured according to the invention.

The basic concept of periodontal measurement according to the invention is illustrated in FIGS. 1 and 2, where a tooth 24 has a crown 25 and a root 26 anchored in jawbone 28. Gum tissue 30 surrounds and abuts the tooth 24 above the jawbone 28. The onset of gum disease such as gingivitis is characterized in the formation of pockets between a tooth and abutting gum tissue. Such a pocket is indicated by reference numeral 32 in FIG. 2 and includes an upper lip 34. Gum attachment is indicated by reference number 35. Gum pocket depth is measured from the top 34 to the bottom 35 of the gingival pocket, while periodontal attachment level is measured from the crown 25 of the tooth 24 to the attachment contour 35, which coincides with the bottom of the gingival pocket. The gingival level is the difference between these two measurements.

According to the invention, the interior of a mouth wherein the tooth 24 is located is bathed in the light issuing from the high-intensity lamp 10, so that the portion of the tooth 24 above the gumline is illuminated. The probe tip 18 is an elongate, blunted needle which is inserted according to conventional periodontal procedures into the pocket 32. For the practice of the invention, the tip 18 has disposed longitudinally on it a linear array 36 of opto-electronic elements. Preferably, the array 36 is a line of serially-connected CCD cells formed on the external surface of the tip core 18. In addition, a collar 38, made of nontransparent material, is slidably disposed on the tip 18 over the array of opto-electronic cells 36. The collar 38 is moved over the array 36 and acts as an optical shield for the array. When the tip 18 is inserted into the pocket 32, the distal end of the tip engages the bottom of the pocket 32. In addition, the optical shield collar 38 engages the crown 25 of the tooth 24, causing the collar 38 to rest in a location on the tip 18 corresponding to the location of the crown 25. When the tip 18 is positioned as illustrated in FIG. 2, the illumination causes at least two discernible dark-light transitions to be indicated by the array 36. The first occurs at a location corresponding to the top 34 of the gingival pocket 32, the other at the location of the optical shield collar 38. It will be evident that, if the length of the array 36 is known, the depth of the pocket 32 can be directly derived from the first dark-light transition on the array 36, while the attachment depth corresponds to the distance between the distal end of the array 36 and the dark-light transition caused by the collar 38.

Figure 3:
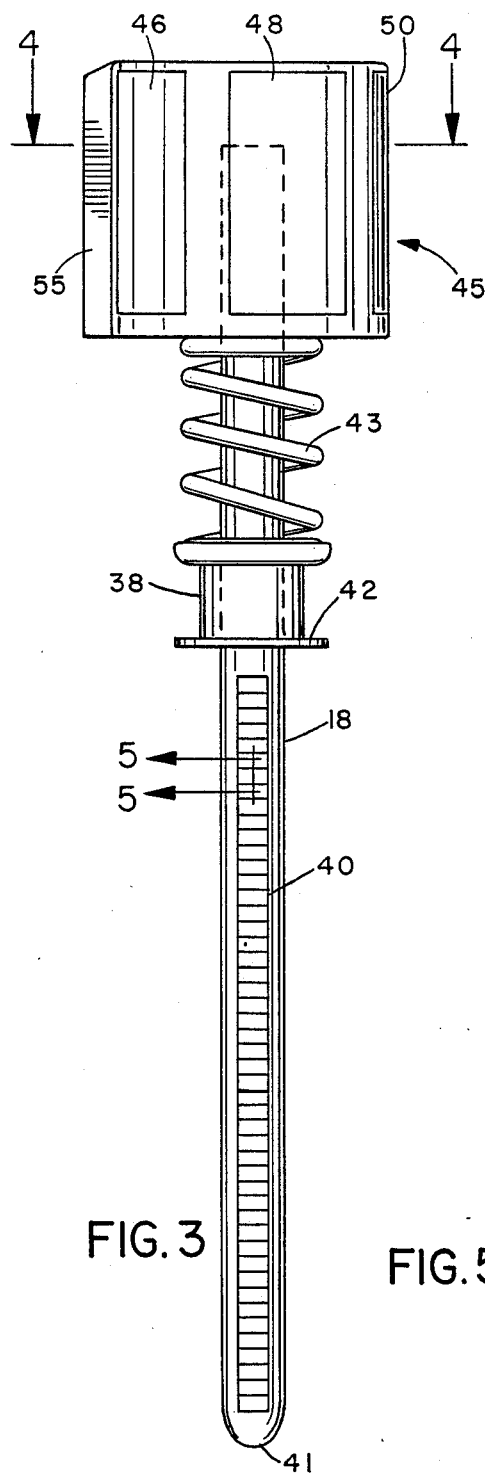
FIG. 3 is a plan view illustrating a periodontal probe tip constructed to perform periodontal pocket depth and periodontal attachment level simultaneously.
Figure 4:
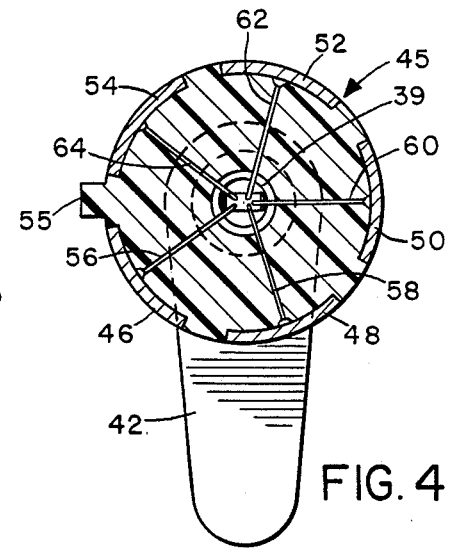
FIG. 4 is a top plan view illustrating an electrical contact arrangement on the probe tip of FIG. 3.
Figure 5:
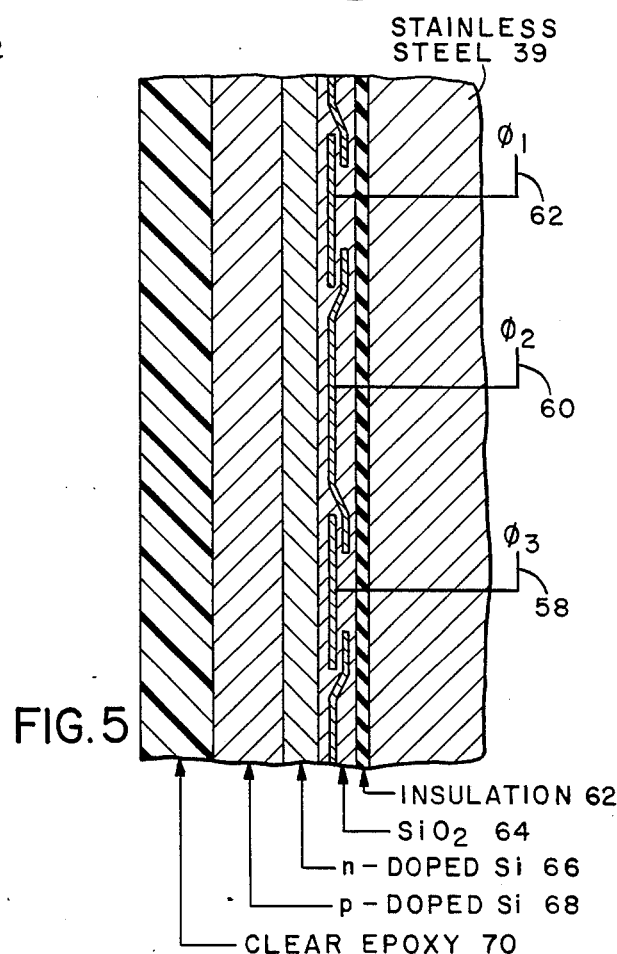
FIG. 5 is a magnified partial sectional view illustrating the structure of an element in the CCD array on the probe tip illustrated in FIG. 3.

FIGS. 3–5 illustrate a preferred structure combining the probe tip, opto-electronic element array, and crown engagement collar that is appropriate for practicing the invention. These figures illustrate the design of a charge-coupled device (CCD) implementation of the opto-electronic element array. In this instantiation, the probe consists of a stainless steel needle (reference numeral 39 in FIG. 5) on which a linear sequence 40 of serially-connected CCD cells is formed. The linear CCD array extends longitudinally from the distal end 41 to the far end of the probe tip. The optical shield includes the slidable collar 38, a member 42 attached radially to the lower edge of the collar 38, and a spring 43 which connects and acts between the collar 38 and a keyed endpiece 45. The keyed endpiece 45 is attached to the far end of the probe tip. The keyed endpiece includes five longitudinal electrical contacts 46, 48, 50, 52, and 54. Reference numeral 55 indicates the key of the endpiece. The key adapts the endpiece for being received into a receptacle in the probe end 16 in such a manner as to orient the contacts 46, 48, 50, 52, and 54 with corresponding contacts in the receptacle. The contacts on the keyed endpiece connect to respective electrical signal conductors 56, 58, 60, 62, and 64. The conductors 56 and 64 carry a signal connection and ground, respectively, to the CCD array 40. The conductors 58, 60, and 62 provide three clocking voltages $\phi 3$, $\phi 2$, and $\phi 1$, respectively. The individual cells of the array 40 have the form illustrated in FIG. 5.

FIG. 5 illustrates one cell of the array 40 in structural detail. The cell is formed on stainless steel needle 39 by conventional deposition techniques conducted against a substrate of insulating material 62 formed on the exterior surface of the core needle 39. The cell is formed in a layer of silicon dioxide ($SiO_2$) 64. Overlayers of, first, n-doped silicon 66 and, second, a layer of p-doped silicon 68. The array 40—and the entire probe 18—is ensheathed in a continuous layer of clear epoxy 70. The epoxy layer 70 insulates the array 40 and provides the blunt, rounded profile of the probe distal tip 41.

As illustrated in FIG. 5, each individual cell of the array 40 receives the three phased clock voltages by individual taps from the conductors 58, 60, and 62. Preferably, these conductors are contained in the insulation layer 62, but are broken out into the stainless steel core 39 in FIG. 5 simply for purposes of illustrating how the individual cell represented by this Figure operates.

The array 40 is operated in conventional three-phase CCD array format. However, other linear array configurations (such as virtual-phase CCD and photodiode) are also possible, and are included within the scope of these teachings. For the three-phase array illustrated, each individual cell in the array 40 consists of three overlapped gates that induce a potential profile within the silicon structure of which the array is formed. By operating the three clocks ($\phi 1$, $\phi 2$, and $\phi 3$) in proper sequence, the photo-electron "packet" in each array cell is transferred to the adjacent cell, and thus the entire array contents can be clocked out of the array in serial fashion, providing an indication of the accumulated charge in each element. As is known, the charge in each element is directly proportional to the light intensity falling on the element. Although the array is illustrated as lying on only one side of the probe 18, it is contemplated that the array may be duplicated on the opposite side of the probe 18, using the same electrode gate connections, if required to provide good azimuthal coverage.

Periodontal pocket depth sensing is accomplished by the structure of FIGS. 3-5 by determining the point along the array 40 at which the transition occurs from dark (that is, below the gumline) to light. The length of the array 40 is known; therefore, the portion of the array which is darkened by the gum pocket can be determined from the dark-to-light transition, and directly converted into a measurement of the gum pocket depth. Periodontal attachment level is sensed by the spring-loaded collar 38, whose lower edge is projected by the radial member 42. The member 42, resting on the crown of a tooth, causes the collar 38 to cover a section of the array 40, thereby darkening the underlying elements. Again, the location of the dark-light transition caused by the lower edge of the collar 38 is directly indicative of the attachment level, which is the length of the array 40 from the lower edge of the collar 38 to the end of the array adjacent the distal tip 41. It is noted that the spring 43 will also cast shadows on the array 40. However, the processing of the output of the array 40 will search for a first darkened portion corresponding to the height of the collar 38. The collar height 38 is greater than, and therefore distinguishable from, the shadows cast by the coils of the spring 43. The position of the collar 38 is therefore not obscured by the dark-light transitions resulting from the shadows cast by the spring 43.

Figure 6:
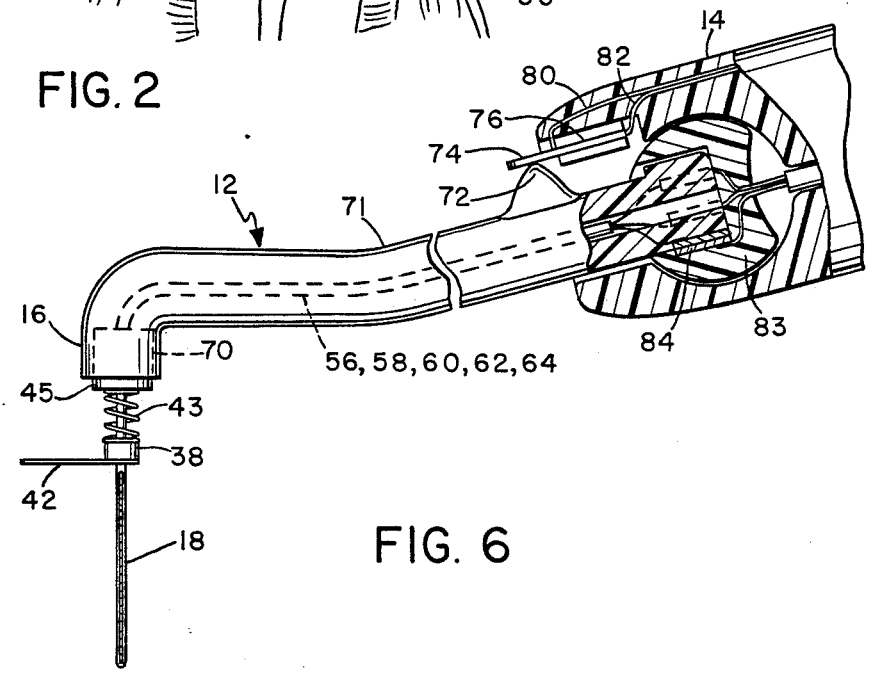
FIG. 6 is a side view illustrating the forward end of a periodontal probe equipped with a pressure sensor and a tip corresponding to the probe tip illustrated in FIG. 3.

FIG. 6 illustrates the interconnection of the probe tip 18 constructed as illustrated in FIGS. 3-5, with the probe handle 14. The keyed endpiece 45 of the probe tip 18 is received in a correspondingly-keyed receptacle 70 at one end of a probe tip carrier 71. The endpiece 45 is received in the proper orientation in the receptacle 70 by the seating of the key 55 in a corresponding key slot (not shown) in the receptacle 70. The receptacle 70 has electrical contacts (not shown) which form respective continuous electrical conductive parths with the contacts on the keyed end 45. The receptacle 70 is fixed to the end 16 of the probe 12. The keyed end 45 of the probe tip is slidably receivable in the receptacle 70 and is held there by conventional releasable retention means for so long as the probe is employed for conducting a periodontal examination. When the examination is completed, the probe is removed from the receptacle 70 and dispoed of, to be replaced by another probe for another examination. Disposability of the probe tip assists in reducing the spread of communicable disease. Alternatively, the probe tip can be fixedly attached to the probe end and sterilized after each use.

The probe tip carrier 71 is moveably connected to the distal end of the probe handle 14 by a keyed ball and socket assembly 83, rotatably held in the end of the probe handle 14. Electrical connection between the handle 14 and tip carrier 71 is provided by keyed electrical contacts 84 in the tip carrier and ball and socket 83.

The handle portion 14 of the probe includes structure for sensing a pressure applied on the probe tip 18. The purpose of the pressure sensing is summarized in U.S. Pat. No. 4,340,069, of Yeaple. In essence, the object of pressure sensing is to determine when the probing force applied to the probe 18 reaches a predetermined magnitude. The predetermined magnitude corresponds to a level beyond which there is danger of penetrating the bottom of a gum pocket. The level also provides a baseline which ensures that the plurality of measurements made during examination are uniformly executed against a single pressure reference. The Yeaple patent features a pressure sensor comprising a magnetized separable sensor having two portions held together by a magnetic force which is overcome when the predetermined force level is exceeded. In order to reduce the number of moving parts and therefore the mechanical complexity of the probe used in the system of the invention, force sensing is accomplished by a projection member 72 on the probe tip carrier 71, a flexible metal reed 74 resting on the projection member 72, and a strain gauge 76 which measures the flexure of the reed 74. The strain gauge 76 is attached to the inside of the distal end of the probe handle 14. However, it is well within the scope of the invention to provide a force sensing mechanism which is external to the handle 14.

FIG. 6 is merely illustrative of an easily-understood force sensor.

The magnitude of the force existing on the probe tip is measured by the strain gauge 76, the level being indicated as a variable differential voltage between the signal conductors 80 and 82. For example, the strain gauge 76 can comprise material whose resistance varies with the flexure of the reed 74, which would cause a detectable change in voltage drop between the conductors 80 and 82, assuming the provision of a constant current through the conductors. Internal to the probe handle 14 is a bundle of signal conductors for transferring signals to and from the probe tip 18 and to and from the strain gauge 76. The conductors 56, 58, 60, 62, and 64 in the probe tip carrier 71 are joined by the conductors 80 and 82. This provides signal conductivity through the handle 14.

Figure 7:
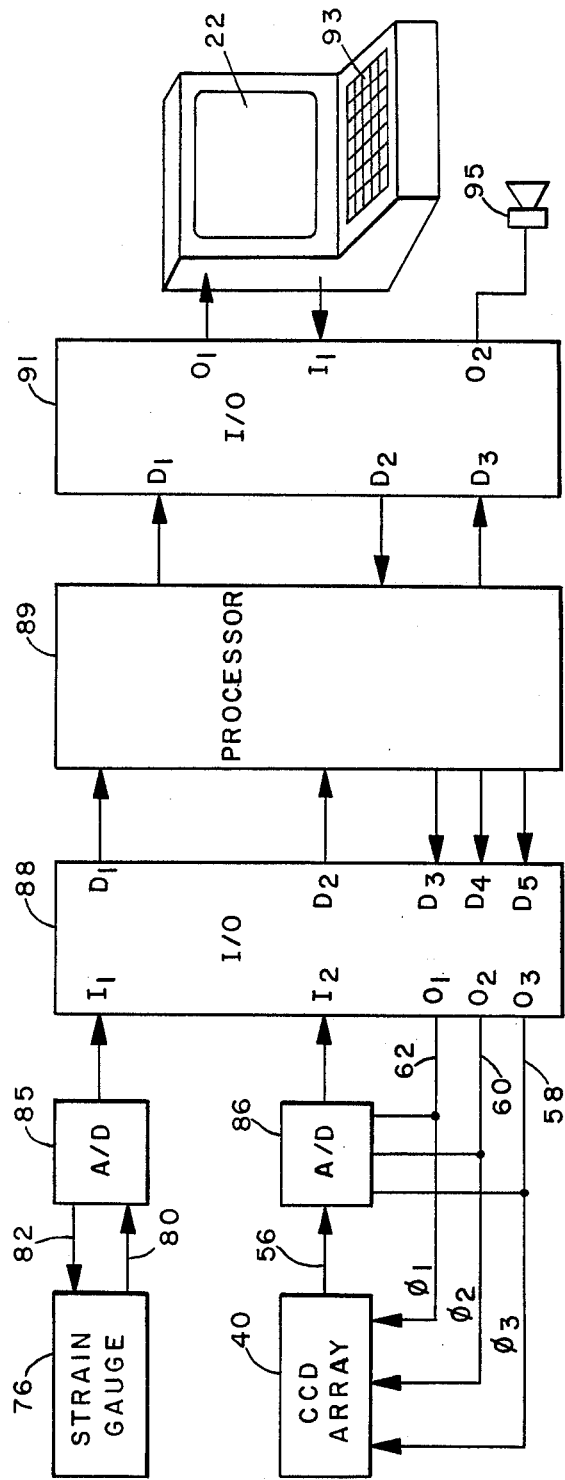
FIG. 7 is a system block diagram illustrating the principal functional blocks of the invention and their interconnection.

The signals provided by the strain gauge 76 and the array 40 on the probe tip are processed by a signal processing arrangement illustrated in FIG. 7. In FIG. 7, a first analog-to-digital (A/D) converter 85 and second A/D converter 86 are connected to an input-output (I/O) interface 88. The I/O interface and a second I/O interface 91 provide input/output channels for a microprocessor 89. The I/O interface 88 provides channels between the processor 89 and the strain gauge 76 and CCD array 40. The I/O interface 91 serves to channelize the flow of data between the processor 89 and the display 22. As illustrated in FIG. 7, the I/O interface also channelizes data flow between a conventional alpha-numeric keyboard 93 and an output device 95 which provides an audible tone. All of the components illustrated in FIG. 7, with the exception of the strain gauge and CCD array can be located adjacent to or in the chassis of the processor 20 (FIG. 1). Alternatively, miniaturized circuitry can be employed to locate the A/D function in the handle of the probe 14.

Figure 8:
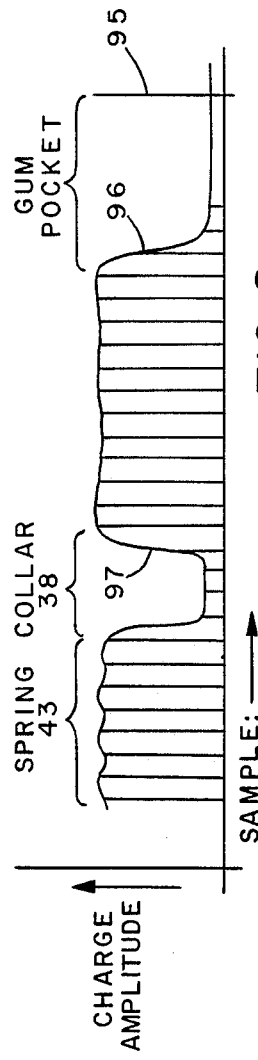
FIG. 8 is a signal diagram illustrating sample depth signals obtained from a probe such as that illustrated in FIG. 3.

In the signal processor illustrated in FIG. 7, the A/D converter 85 operates conventionally to continuously sense, convert, and provide to the processor 89 the voltage dropped by the strain gauge 76. This furnishes a continuous digital representation of the voltage on the strain gauge 76, which is converted by conventional software means in the processor 89 to a force magnitude. The A/D converter 86 is synchronized by the three phase voltages on signal lines 58, 60 and 62 with the signal stream provided by the CCD array 40. The CCD array 40 provides a signal string comprising a sequence of charge levels accumulated by the individual elements of the array 40. The string is provided in the sequence corresponding to the sequence of the array 40, with the top-most element providing the first charge value, and so on, until the last element's charge value is clocked out of the array 40. The first element can be either the element nearest the distal end 41 or the element nearest the keyed endpiece 45. The A/D sampling function is synchronized with the output string of charge values, and provides a corresponding string of multi-bit digital values, each corresponding to a digital representation of a respective charge value input into the converter 86 from the CCD array 40. Thus, the processor 89 receives a string of digital values corresponding to the string of charge values accumulated and output by the CCD array 40. FIG. 8 is a representative waveform illustrating both the charge value string provided to the A/D converter 86 and the digital string provided to the processor 89. The FIG. 8 waveform assumes the first element is adjacent the endpiece 45; the waveform illustrates the envelope connecting the sequence of values in both the charge value and digital value strings. Thus, one the horizontal axis, the sample chronology is laid out with the first sample (taken from the first array element) nearest the vertical axis, and the last sample indicated by the vertical line 95. The charge amplitude of the samples is represented by the vertical axis. The charge profile indicates the dark-light transitions on the CCD array 40 caused by, respectively from the left along the horizontal axis, the spring 43, the collar 38, and the periodontal pocket. The length of the CCD array 40 corresponds to the number of elements in the array and thus is proportional to the distance between the vertical axis and the vertical line 95. The depth and level dimensions of interest in a measurement are directly obtainable from the waveform of FIG. 8. Thus, the pocket depth is represented by the distance between the waveform dark-light transition 96 cause by the periodontal pocket, while the attachment level is directly obtainable from the right-hand transition 97 in the portion of the waveform representing the shadow of the collar 38. Gingival level is the illuminated portion between the transitions 97 and 96. FIG. 8 is thus representative of the derivation in a single processing step of the three measurements of interest: pocket depth, gingival level, and attachment level.

The processor 89 is conventionally programmed to process the charge profile obtained from the CCD array in response to the pressure signal provided by the strain gauge 76. In summary, the processing consists of the processor 89 continuously monitoring the magnitude of the force signal provided by the strain gauge 76. When the monitored force signal ascends to the predetermined value, the processor 89 provides the voltage phase signals to the CCD array 40 to clock out the charge profile. As the charge profile is clocked out and converted by the converter 86, the processor 89 accumulates the digital representation of the charge profile and obtains the location of the illumination transition caused by the lower edge of the collar 38 as well as the location of the transition caused by the edge of the periodontal pocket. The two locations are then transformed with reference to the known length of the CCD array 40 into the respective attachment level and pocket depth. Gingival level is obtained by determination of the distance between the transitions.

The processor 89 is also appropriately programmed to direct the particular in conducting a periodontal examination by means of a dental chart display output by the processor through the display 22. The processor 89 also accumulates measurement values in the predetermined sequence in the format of a dental examination record which the processor retains in stored for the purpose of displaying the results of a current examination and also for the purpose of maintaining a periodontal history of a patient. Further, the processor 89 is enabled to compare the results of any two periodontal examinations for the same patient to obtain a record of change, which is extremely useful in diagnosing and monitoring the progress of periodontal disease.

The first function, the direction of the practitioner in conducting an examination, is now summarized. A systematized sequence of periodontal measurements is indicated by the processor 89 via the display 22 in a dental chart format showing mesial, distal, lingual, occlusal, and buccal views of the upper and lower dental plates. In FIG. 10A, the teeth of the lower plate are represented in all of these views from the bottom of top of the Figure. The examination guidance procedure of the processor 89 consists of positioning a visible indicator at each of the customary measurement sites around each tooth in the upper and lower plates. As is known in periodontal practice, the number of sites can vary from 12 for certain molars, to six for the upper and lower front teeth. The examination is systematized by directing the practitioner in a sequence beginning on the lingual side 100 of the left lower molar and progressing sequentially along the lingual aspect from left to right and then the buccal aspect from right to left of the lower plate, followed by the same sequence on the upper plate. The sequence is prompted by the display of a marker 105 at the next measurement site. The marker 105 consists of a circle enclosing a number and positioned at the site where the measurement is to be performed. The enclosed number is one in a sequence of 1-6 and indicates the position of the next performed measurement relative to the first measurement on the indicated tooth and view. The number is referred to as the "station number," with "station" corresponding to "measurement site."

The sequence is shown on the occlusal view of the teeth being measured; it is initiated by displaying the marker at station 1 in FIGS. 10A and 10B and then moving the marker to station 2 when the measurement at station 1 is completed. The measurement seequence prompt continues as described and ends, for the lower plate, at measurement position 144. Thus, each time the practitioner makes a measurement, the processor 89 responds to the predetermined magnitude of the strain gauge signal, operates the CCD array, processes the signal string from the A/D converter 86, and moves the station marker from the present measurement site to the next. Movemvent of the marker is apparent visually on the screen 22. In order to concentrate the practitioner's attention on the measurement sequence and to prevent exertion of a perilous level of pressure, an audible tone is provided through the output device 95 each time a measurement is made and the marker is moved.

Variations in dental topography from patient to patient are accommodated in the periodontal examination sequence programming. Thus, the sequence is based upon a display of thirty-two teeth, the normal expected complement. Further, the sequence is initiated by moving the marker to a default position on the lingual aspect of the lefthand molar of the lower plate in the full complement. However, provision is made for advancing the dot in response to keyboard commands entered on the keyboard 93 by the practitioner. Thus, less than a full complement of teeth and gaps in a respective dental topography can be accommodated by the sequence function of the system of the invention.

Figure 11:
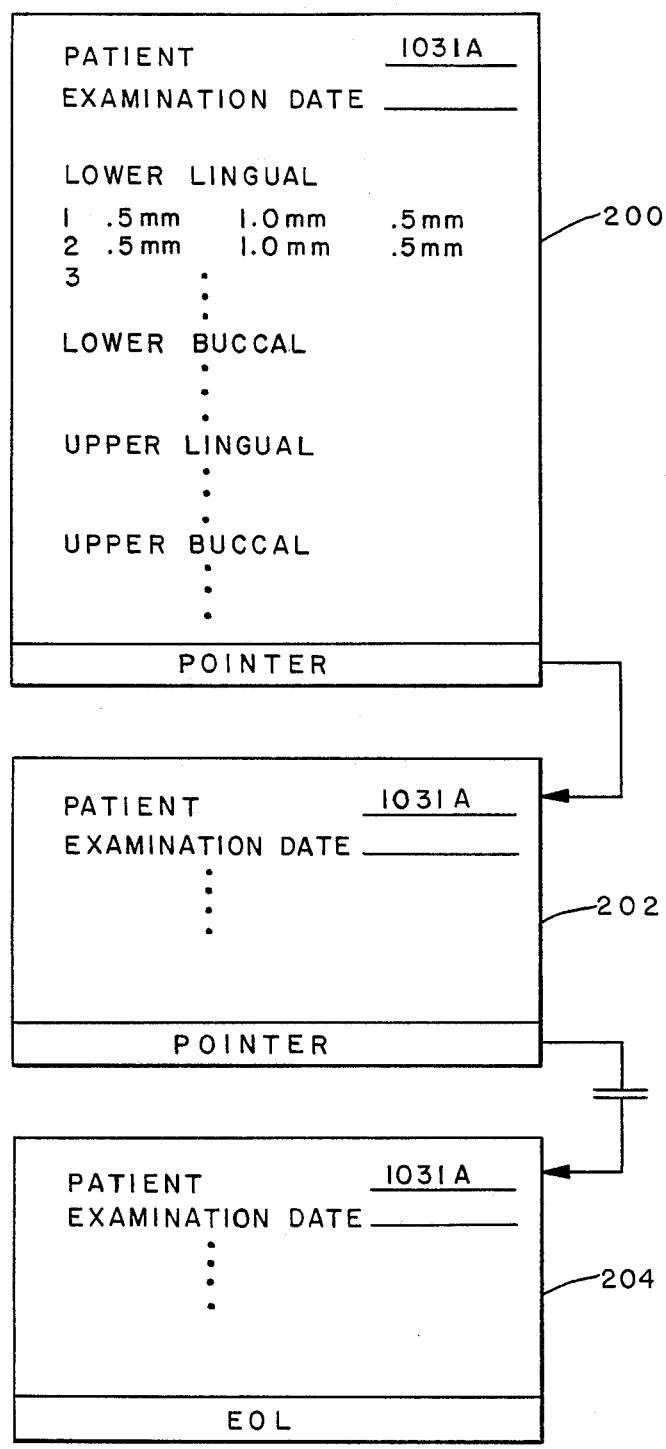
FIG. 11 illustrates how measurement files are structured and stored.

FIG. 11 illustrates the recordkeeping format employed by the system of the invention. In FIG. 11 a series of files are shown in conventional linked-list format, with the linked-list representing the periodontal examination history of a patient. File 200 illustrates both how the results of a currently-conducted examination are accumulated and the examination first format of the completed examination. In this regard, the file 220 is only representational in that it corresponds to a record kept in digital format in the storage processor 89. However, or purposes of understanding the accumulation of periodontal measurement data, the file 220 is identified by a patient number and examination date and includes individual entries. Each entry corresponds to a probe measurement site corresponding to a respective station in the sequence display. Thus, for example, station 1 has a corresponding record in the examination file 220. The file record has stored at marker location 110 the pocket depth and attachment and gingival level measurements obtained at the corresponding probe site. The file 200 is accumulated record-by-record as a periodontal examination is made according to the sequence represented by FIGS. 10A and 10B. When the sequence is completed, and the file 200 is full, the file is terminated by a pointer to the next most recent examination file for the same patient. Thus, the files 200, 202, and 204 represent the complete periodontal examination history for patient 1031A.

FIG. 10B is also illustrative of representation of the results of a periodontal examination and also of the display of results of comparing two periodontal examinations. In summary, the procedure for displaying the results of a current periodontal examination consist of drawing on the lingual and buccal views of the lower and upper plates a pair of lines on each tooth, the lower indicating attachment location and the upper the pocket lip. Thus in FIG. 10B, the lingual view of the lower plate shows a first line sequence 210 representing the elevation envelope of attachment locations obtained for the lingual aspect of the lower plate. The upper line sequence 212 represents an elevation line corresponding to the upper pocket edges of the same teeth. In an examination being conducted or just completed, the processor 89 provides the display of FIG. 10B through the output display 22 and employs graphics means to draw the lines on the dental format displays,. The line sequences 210 and 212 are drawn in response to direct conversion of the measurement values obtained for each tooth in the above-described examination sequence.

FIG. 10C is representative of a comparison function which uses a pair of periodontal examination files obtained from the history of a particular patient to display changes in measurement. In this regard, the lines 214 represent the differences between the pocket depths of, for example, the file 202 and the file 200. To obtain the profiles for the lines 214, the processor 89 simply subtracts on a record-by-record basis the corresponding probe measurements for each tooth in the two files. As illustrated, the comparison function displays results on the occlusal map by drawing, at each station, a line whose length represents the magnitude of difference between the pocket depths measured at the station. The line is colored appropriately to indicate the direction of change: that is, the color of the line indicates whether the depth has increased or decreased.

Figure 9:
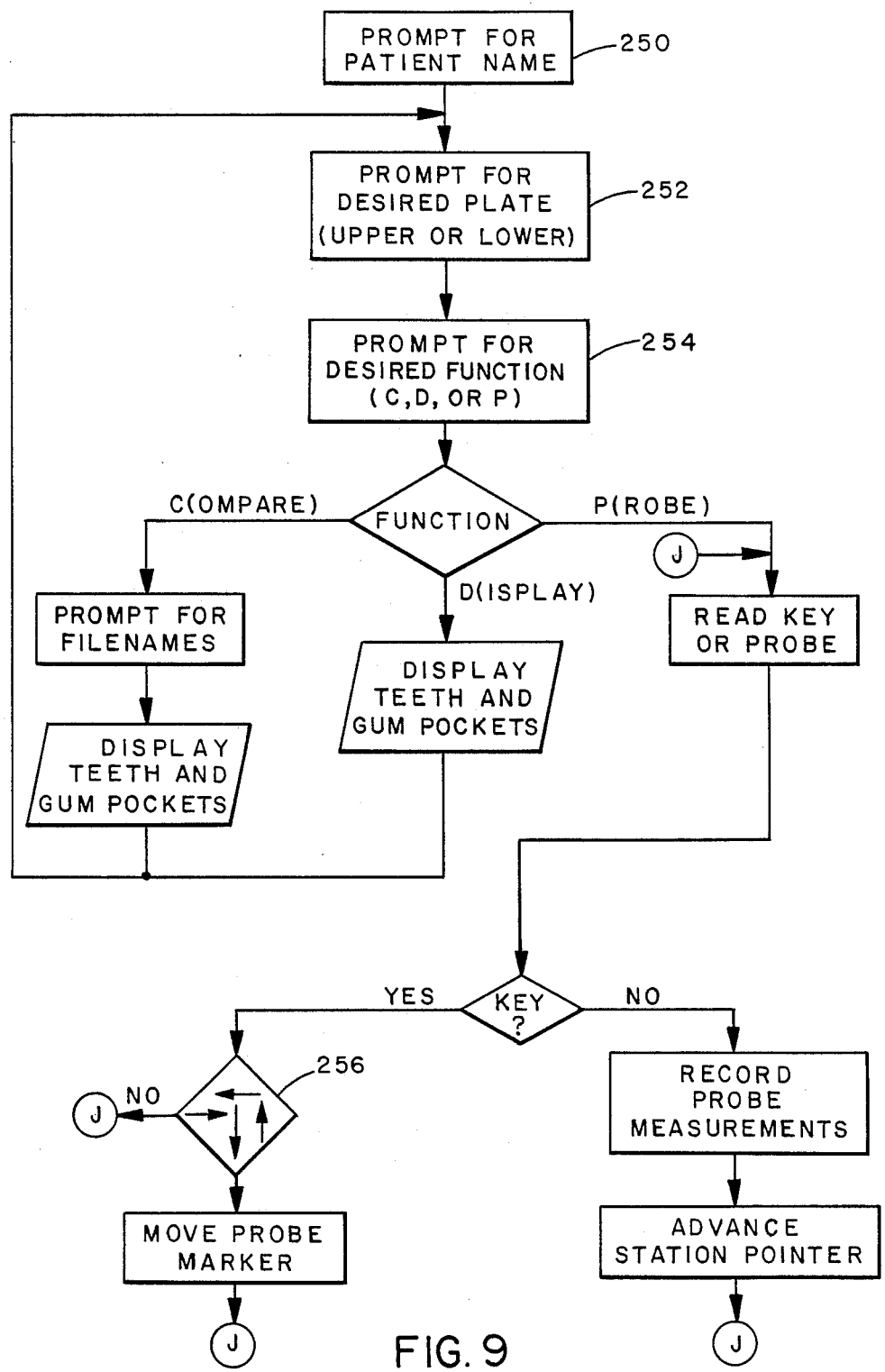
FIG. 9 is a process flow diagram illustrating how measurements obtained with the probe illustrated in FIG. 3 are processed according to the invention.

The processing functions undertaken by the processor 89 are illustrated in flow diagram form in FIG. 9. Thus, when the probe system is initially activated by conventional initialization exchange 250 between the operator and the processor 89 via the display 22 and alpha-numeric keyboard 93, the processor 89 prompts for the name of the patient being examined. Next, the practitioner selects in step 252 for display either the upper or the lower plate of the patient prompted for. This sets the basic display format for all of the processing functions performed by the processor 89. Next, the function desired is selected in step 254 by the operator in response to a system prompt. The functions are denoted as P (for probe measurement), D (for displaying measurement results), or C (for displaying the results of comparison of two examination files). The P function is initialized by displaying the station marker at the lefthand-most station on the lingual view of the lefthand-most tooth of the selected plate, and testing for a response either from the alpha-numeric keyboard or the periodontal probe. The keyboard command is in the form of a cursor control function 256. In the normal keyboard arrangement, this is provided by one of four cursor movement command keys with an arrow pointing in one of four orthogonal directions. If the horizontal movement command is input, the marker is moved corespondingly to the adjacent tooth on the view where the marker is located. If a vertical movement command is entered, the marker is moved to the first station of the opposite view of the tooth. If no keyboard command is received, then, when a predetermined force magnitude is reached and the probe measurements are obtained and converted (in step 258), the measurements being recorded in the formats described above. When the measurements are recorded for the indicated station, the marker is advanced to the next measurement station. The P function is terminated when the escape key is depressed. Values for stations that have been probed a second time will overwrite previous measurements in the file.

The D function is entered by a keyboard command and operates by displaying an examination file in the format of FIGS. 10A and 10B without the station marker. Selection of the C function consists of prompts to the operator for the names of files to be compared. Upon receiving the file names, the comparison function is executed, the results being displayed in the format described above and illustrated in FIG. 10C.

A practice of the procedure illustrated in FIG. 9 can be understood with reference to the tables wherein software program functions implementing the processing functions described above and illustrated in FIG. 9 are presented in conventionally-understood pseudo-code format. As is known, pseudo-code is an abstract functional expression from which appropriate computer programs can be derived in selected languages. Therefore, an application program executable on a processor and expressed in a selected language can be derived from the following tables.

In the MAIN function (Table I), the three prompts leading to the functional selection are provided. Thus, in lines 111–116, the patient name is used to either obtain or create a measurement file. In lines 118–134, the plate to be displayed in the formats of FIGS. 10A and 10B is selected, a workfile (pm) for current work is opened and assigned to the selected plate. Lines 134–140 prompt for the desired function. The functions comprise one or more callable routines described below. The P function is called by the name "PROBE," while the D function includes the called functions "DRAW TEETH" (Table VIII) and "DRAW POCKET" (Table III). The D function first uses the DRAW TEETH function to draw the dental chart including lingual, occlusal, and buccal views of the selected plate and then, for both the lingual and buccal views of each tooth, fills the pocket between the two lines in FIG. 10B, using the DRAW POCKET function. The C function (lines 153–187) obtains and reads the first and second measurement files which are to be compared, draws the dental chart for the selected plate, assigns a false value ot a FILL FLAG, reads the first measurement file into array "pm1" and draws in blue the pockets for the pm1 array. The function next reads the second file into an array "pm2" and draws those pockets in red. Finally, the function "SHOW DIFFS" (Table X) is called which calculates and draws the pocket depth change dimensions in the format described above on the occlusal view for the plate.

Returning to the P function, the practitioner performing a current set of measurements invokes the P function by an appropriate command key, and the Table I code portion calls the function denoted as PROBE. The PROBE function is embodied in the pseudo-code of Table IX wherein the DRAW TEETH function (Table VIII) is called, the selected plate is drawn on the screen and the GET STN PARS function (Table II) is called to identify the first measurement site (station) on the first tooth in the measurement sequence. In the GET STN PARS function, the probe measurement parameters are denoted as "np" (plate number, with 1 = upper, and 2 = lower), "stn" (measurement station number), and "nv" (view number, with 1 = lingual, and 2 = buccal). The function "MARK" (Table IV) is called to draw the probe marker at the first measurement station of the first tooth. The MARK function moves the mark in its predetermined sequence through the measurement stations. Recall that each view of a tooth has three or more measurement stations and that the stations are taken in sequence, left to right on the lingual aspect, right to left on the buccal. While moving the marker from station to station, the MARK function also draws the appropriate digit for the current measurement station on the occlusal view and draws a circle around the digit.

Once the PROBE function is initialized, it employs a repeat loop calling, in sequence, READ PROBE to read the probe in the manner described above and increment the station number, MARK to erase the mark on the station where the probe is currently measuring, GET STN PARS to update the tooth and view, and then, once again, MARK to mark the updated station. This loop embodies the predetermined measurement sequence.

The probe measurement sequence loop initially continuously reads the strain gauge voltage to determine the pressure exerted on the probe tip. When the pressure magnitude reaches the predetermined threshold, the READ PROBE function is called. The READ PROBE function first invokes the "CONVERT" function (Table VI) which performs A/D conversion of the probe measurement via the A/D converter 86. The digital string resulting from the conversion is scaled by the READ PROBE function and the pocket and attachment depths are obtained by scaling the converted digital values as discussed previously. The scaled values are placed in a current probe measurement ("PM") file which stores, for each plate, in each station location the distance from the crown of the tooth to the bottom of the gum pocket and the distance from the crown of the tooth to the top of the gum pocket. The "stn" parameter is sampled and if the station just measured is the end station for the tooth, the DRAW POCKET function is called to draw the pocket for the current view of the tooth. During the execution of the PROBE function, the D parameter will have a value which will cause the DRAW POCKET routine to draw only one pocket per tooth view. Next in the PROBE measurement sequence loop, MARK is called to erase the marker on the location just measured. If the marker is erased from the last station, the measurement sequence is complete, and the current file of the completed measurements is stored in the list containing the patient's files. Otherwise, the station parameters are updated to the next station and the marker is moved to reflect the updated parameters.

Provision is also made for reading keyboard entries by way of the function "READ KEY" (Table V). This function moves the mark in response to cursor control commands from the keyboard.

TABLE I

```
        Function MAIN;
110     read digit fonts for graphics display;
111     prompt for patient name;
112     read patient name;
113     if (patient probe measurement file exists)
114        open patient probe measurement file;
115        read probe measurements;
116     end if;
117     repeat
118        prompt for U(pper plate), L(ower plate), of Esc(ape);
119        wait for keystroke;
120        read command character, 'ch';
121        if ('ch' not in {U, L, Esc})
122           next;
123        if ('ch' = Esc)
124           break from repeat loop;
125        if ('ch' = U)
126           assign work_file to upper plate picture file;
127           np = 1;
128        if ('ch' = L)
129           assign work_file to lower plate picture file;
130           np = 2;
131        open work_file;
132        read upper or lower plate picture file from work_file;
133        close work_file;
134        repeat
135           prompt for C(ompare), D(isplay) or P(robe) function
                 command;
136           wait for keystroke;
137           read function character, 'ch';
138           if ('ch' in {C, D, P})
139              break from repeat loop;
140        end repeat;
141        if ('ch' = P)
142           call function PROBE;
143        if ('ch' = D)
144           call function DRAW_TEETH;
145           color = red;
146           for (nt = 1 to 16)
147              for (nv = 1 to 2)
148                 call function DRAW_POCKET;
149              end for;
150           end for;
151           wait for keystroke;
152        end if;
153        if ('ch' = C)
154           prompt for first probe measurement file name;
155           read first probe measurement file name;
156           prompt for second probe measurement file name;
157           read second probe measurement file name;
158           if (both filenames exist)
159              call function DRAW_TEETH;
160              fill_flag = false;
161              assign meas_file to first measurement file name;
162              open meas_file;
163              read meas_file values into array 'pm1';
164              close meas_file;
165              color = blue;
166              for (nt = 1 to 16)
167                 for (nv = 1 to 2)
168                    call function DRAW_POCKET with 'pm1';
169                 end for;
170              end for;
171              read meas_file values into array 'pm2';
172              close meas_file;
173              color = red;
174              for (nt = 1 to 16)
175                 for (nv = 1 to 2)
176                    call function DRAW_POCKET with 'pm2';
177                 end for;
178              end for;
179              call function SHOW_DIFFS;
180              wait for keystroke;
181              fill_flag = true;
182           else
183              notify user that file names don't exist
184           end if;
```

TABLE I-continued

```
185           end if;
186        end repeat;
187     end of MAIN;
```

TABLE II

```
Function GET_STN_PARS;
!
! given the current plate and probe station number, this
! routine finds the corresponding tooth and view;
!
   if (np = 1)
      if (stn < 49)
         nv = 1;
      else
         nv = 2;
      end if;
   end if;
   if (np = 2)
      if (stn < 67)
         nv = 1;
      else
         nv = 2;
      end if;
   end if;
   nt = stn_tooth[np, stn];
end of function GET_STN_PARS;
```

TABLE III

```
Function DRAW_POCKET;
!
! given the current plate and tooth, this routine draws the gum
! pocket using the values in the probe measurement file; if the
! fill_flag is true, the gum pocket is filled with the color
! specified by the value of 'color';
!
   st_stn = start_stn[np, nv, nt];
   en_stn = end_stn[np, nv, nt];
   ns    = en_stn - st_stn + 1;
   if (nv = 1)
      nsl = st_stn;
      nsr = en_stn;
   else
      nsl = en_stn;
      nsr = st_stn;
   end if;
   if (np = 1)
      nr   = llc_row[1, nv+1, nt];
      nrlb = nr - 2 * pm[1, nsl, 1];
      nrrb = nr - 2 * pm[1, nsr, 1];
   else
      nr   = llc_row[2, nv, nt];
      nrlt = nr + 2 * pm[2, nsl, 1];
      nrrt = nr + 2 * pm[2, nsr, 1];
      nrlb = nr + 2 * pm[2, nsl, 2];
      nrrb = nr + 2 * pm[2, nsr, 2];
   end if;
! find left side of higher pocket end on current tooth;
   nc = llc_col[np, nt]
   while (get_dot_color(nc, nrlt) = black)
      nc = nc + 1;
   end while;
   nclt = nc;

! find right side of higher pocket end on current tooth;
   nc = llc_col[np, nt] + twid[np, nt] - 1;
   while (get_dot_color(nc, nrrt) = black)
      nc = nc + 1;
   end while;
   ncrt = nc;

! draw higher pocket end on current tooth;
   ncols = ncrt - nclt;
   step = ncols / (ns - 1);
   bumps = ncols - (ns - 1) * step;
   if (nv = 1)
      ncl = nclt;
   else
      ncl = ncrt;
```

TABLE III-continued

```
end if;
bump = 0;
for (st = st_stn to en_stn - 1)
    if (np = 1)
        nr = 11c_row[1, nv+1, nt];
        nr1 = nr - 2 * pm[1, st, 2];
        nr2 = nr - 2 * pm[1, st+1, 2];
    else
        nr = 11c_row[2, nv, nt] - thit[2, nv, nt];
        nr1 = nr - 2 * pm[2, st, 2];
        nr2 = nr - 2 * pm[2, st+1, 2];
    end if;
    offset = step;
    if (bump < bumps)
        offset = offset + 1;
    end if;
    if (nv = 2)
        offset = -offset;
    end if;
    nc2 = nc1 + offset;
    draw line in 'color' connecting (nc1, nr1) and (nc2, nr2);
    nc1 = nc2;
    bump = bump + 1;
end for;

! find left side of lower pocket end on current tooth;
nc = 11c_col[np, nt];
while (get_dot_color(nc, nr1b) is black)
    nc = nc + 1;
end while;

! find right side of lower pocket end on current tooth;
nc = 11c_col[np, nt] + twid[np, nt] - 1;
while (get_dot_color(nc, nrrb) is black)
    nc = nc - 1;
end while;
ncrb = nc;
! draw lower pocket end on current tooth;
ncols = ncrb - nc1b;
step = ncols / (ns - 1);
bumps = ncols - (ns - 1) * step
if (nv = 1)
    nc1 = nc1b;
else
    nc1 = ncrb;
end if;
bump = 0;
for (st = st_stn to en_stn - 1)
    if (np = 1)
        nr = 11c_row[1, nv+1, nt];
        nr1 = nr - 2 * pm[1, st, 2];
        nr2 = nr - 2 * pm[1, st+1, 2];
    else
        nr = 11c_row[2, nv, nt] - thit[2, nv, nt];
        nr1 = nr - 2 * pm[2, st, 2];
        nr2 = nr - 2 * pm[2, st+1, 2];
    end if;
    offset = step;
    if (bump < bumps)
        offset = offset + 1;
    end if;
    if (nv = 2)
        offset = -offset;
    end if;
    nc2 = nc1 + offset;
    draw line in 'color' connecting (nc1, nr1) and (nc2, nr2);
    nc1 = nc2;
    bump = bump +1;
end for;

! fill gum pocket;
if (fill_flag is true)

! left side
    for (nr = nr1b to nr1t)
        nc = 11c_col[np, nt];
        while (get_dot_color(nc, nr) is black)
            nc = nc + 1;
        end while;
        plot point (nc, nr) in red;
    end for;
```

TABLE III-continued

```
! right side
for (nr = nrrb to nrrt)
    nc = 11c_col[np, nt] + twid[np, nt];
    while (get_dot_color(nc, nr) is black)
        nc = nc - 1;
    end while;
    plot point (nc, nr) in red;
end for;
nrb = 11c_row[1, nv+1, nt];
nrt = nrb - thit[1, nv+1, nt];
else
    nrb = 11c_row[2, nv, nt];
    nrt = nrb - thit[2, nv, nt];
end if;
for (nc = 11c_col[np, nt] to 11c_col[np, nt] + twid[np, nt])
    for (nr = nrb to nrt)
        if (get_dot_color(nc, nr) is red)
            nrb_red = nr;
            for (nr1 = nrt to nrb_red)
                if (get_dot_color(nc, nr1) is red)
                    nrt_red = nr1;
                    for (nr2 = nrt_red to nrb_red)
                        if (get_dot_color(nc, nr2) is white)
                            plot point (nc, nr2) in red;
                        end if;
                    end for;
                    go to label "next_col";
                end if;
            end for;
        end if;
    end for;
    next_col:
end for;
end of function DRAW_POCKET;
```

TABLE IV

```
Function MARK;
!
! marks the active view, tooth and station;
!
if (np = 1)
    if (nv = 1)
        nr = 11c_row[np, 1, nt] - max_hgt + thit[np, 1, nt] + 7;
    else
        nr = 11c_row[np, 1, nt] - max_hgt - 6;
    end if;
    if (nv = 2)
        nr = 11c_row[np, 3, nt] + 7;
    else
        nr = 11c_row[np, 3, nt] - thit[np, 3, nt] - 6;
    end if;
    if (mark-color = 0)
        erase previous mark;
    else
        draw digit for current station number on occlusal view;
        draw circle around digit;
    end if;
end if;
end of function MARK;
```

TABLE V

```
Function READ_KEY;
!
! reads keystrokes made during the PROBE function;
!
read keyboard character, 'ch';
if ('ch' in {arrows})
    erase current mark;
    else if ('ch' = left arrow and nt > 1)
        nt = nt - 1;
    else if ('ch' = up arrow and nv = 2)
        nv = 1;
    else if ('ch' = down arrow and nv = 1)
        nv = 2;
end if;
stn = start_stn[np, nv, nt];
mark current tooth with initial tooth station;
```

TABLE V-continued

```
    end if;
  end of function READ_KEY;
```

TABLE VI

```
Function CONVERT;
!
! performs A/D conversion of probe measurements;
!
    invoke D/A function;
    scale values read;
  end of function CONVERT;
```

TABLE VII

```
Function READ_PROBE;
!
! reads the probe measurements
!
  call CONVERT;

! find differences between contiguous CCD array measurements;
for (i = 1 to 199)
  CCD_DIFF[i] = CCD_MEAS[i + 1] - CCD_MEAS[i];

! find index of CCD element at top of gum;
GUM_INDEX = 1;
MAX_DIFF = CCD_DIFF[1];
for (i = 2 to MAX_GUM_INDEX)
  if (CCD_DIFF[i] > MAX_DIFF)
    GUM_INDEX = i;
    MAX_DIFF = CCD_DIFF[i];
  end if;
end for;
PM[np, stn, 1] = GUM_INDEX × CCD_DSPMT;

! find index of CCD ! element at probe collar!;
COLLAR_INDEX = i + 20;
MAX_DIFF = CCD_DIFF[i + 20];
for (j = i + 21 to MAX_COLLAR_INDEX)
  if (CCD_DIFF[j] > MAX_DIFF)
    COLLAR_INDEX = j;
    MAX_DIFF = CCD_DIFF[j];
  end if;
end for;
PM[np, stn, 2] = COLLAR_INDEX × CCD_DSPMT;

if (stn = end_stn[np, nv, nt])
  call DRAW_POCKET;
end if;
if (np = 1 and stn < 114)
  stn = stn + 1;
end if;
if (np = 2 and stn < 132)
  stn = stn + 1;
end if;
end of function READ_PROBE;
```

TABLE VIII

```
Function DRAW_TEETH;
!
! displays nominal set of teeth on the screen;
!
  set color graphics mode;
  call picture function to draw tooth picture file;
  reflect left hand side of screen to right hand side;
  end of function DRAW_TEETH;
```

TABLE IX

```
Function PROBE;
!
! provides the user interface to the PROBE function;
!
  call DRAW_TEETH;
  stn = 1;
  call GET_STN_PARS;
```

TABLE IX-continued

```
  call MARK to mark first tooth;
  repeat
    read strain gauge;
    if (reading exceeds threshold)
      call READ_PROBE;
      call MARK to erase mark;
      call GET_STN_PARS;
      call MARK to mark current tooth and station;
    end if;
    if (keystroke)
      call READ_KEY;
    end if;
    if ('ch' = Esc)
      break from repeat loop;
    end if;
  end repeat;
  prompt user for name of new probe measurement file;
  open new probe measurement file;
  write "PM" array to file;
  close file;
  all current readings to file;
  end of function PROBE;
```

TABLE X

```
Function SHOW_DIFFS;
!
! displays differences between probe measurement readings from
! two files on occlusal view of current plate;
!
  for (nv = 1 to 2)
    for (nt = 1 to 16)
      if (np = 1 and nv = 1)
        nr = 11c_row [1, 1, nt] - max_hgt + thit[1, 1, nt] + 2;
        dir = +1;
      end if;
      if (np = 1 and nv = 2)
        nr = 11c_row[1, 1, nt] - max_hgt - 1;
        dir = -1;
      end if;
      if (np = 2 and nv = 1)
        nr = 11c_row[2, 3, nt] + 2;
        dir = +1;
      end if;
      if (np = 2 and nv = 2)
        nr = 11c_row[1, 1, nt] - thit[2, 3, nt] - 1;
        dir = -1;
      end if;
      st_stn = start_stn[np, nv, nt];
      en_stn = end_stn[np, nv, nt];
      ns = en_stn - st_stn + 1;
      nc1 = 11c_col[np, nt] + 1;
      ncr = 11c_col[np, nt] + twid[np, nt] - 2;
      ncols = ncr - nc1;
      step = ncols div (ns - 1);
      bumps = ncols - (ns - 1) * step;
      bump = 0;
      if (nv = 1)
        nc = nc1;
      else
        nc = ncr;
      end if;
      for (st = st_stn to en_stn)
        len = pm1[np, st, 2] - pm1[np, st, 1];
        len = len - (pm2[np, st, 1] - pm2[np, st, 2]);
        if (len > 0)
          color = 1;
        else
          color = 2;
        end if;
        nre = nr + dir * |len|;
      end if;
      offset = step;
      if (bump < bumps)
        offset = offset + 1;
      end if;
      if (nv = 2)
        offset = -offset;
      end if;
      nc = nc + offset;
      bump = bump + 1;
```

TABLE X-continued

```
    end for;
   end for;
  end for;
end of function SHOW_DIFFS;
```

TABLE XI

Data Descriptions:

11c_col --- an array dimensioned 2 × 16, which contains the screen column of the lower lefthand corner of the box in which each tooth is displayed; there are 2 plates (upper and lower) and 16 teeth for each plate;

11c_row --- an array dimensioned 2 × 3 × 16, which contains the screen row of the lower lefthand corner of the box in which each tooth is displayed; there are 2 plates (upper and lower), and 3 views with 16 teeth for each plate;

twid --- an array dimensioned 2 × 16, which contains the pixel width of each tooth; there are 2 plates (upper and lower) with 16 teeth for each plate;

thit --- an array dimensioned 2 × 3 × 16, which contains the pixel height of each tooth; there are 2 plates (upper and lower) with 3 views and 16 teeth for each plate;

start_stn --- an array dimensioned 2 × 2 × 16 contains the number of the probe start station for each tooth; there are 2 plates (upper and lower) with 2 surfaces (lingual and buccal) and 16 teeth for each plate;

end_stn --- an array dimensioned 2 × 2 × 16 which contains the number of the probe end station for each tooth; there are 2 plates (upper and lower) with 2 surfaces (lingual and buccal) and 16 teeth for each plate;

stn_tooth --- an array dimensioned 2 × 132 which contains the tooth number associated with each station; there are 2 plates (upper and lower) with 132 probe stations;

CCD_MEAS --- an array dimensioned 1 × 200 which contains the digitized CCD_measurements element 1 is nearest probe tip;

CCD_DIFF --- an array dimensioned 1 × 199 which contains differences between contiguous elements of the "CCD_MEAS" array;

pm --- an array dimensioned 2 × 144 × 2;
alt-pm --- an array dimensioned 2 × 144 × 2;

Obviously, many variations of the described invention can be practiced without departing from the scope or spirit of the invention. Thus, it is to be understood that the descriptions and illustrations used in te Abstract and Specification do not limit the invention, nor do they exclude equivalents of the characteristics illustrated, described, or claimed. The invention is limited solely by the claims which follow.

We claim:

1. A system for performing periodontal measurements, comprising:
    a probe having a forward end and a handle surface;
    an electrical signal conductor in said probe;
    a pressure sensor in said probe and connected to provide a pressure signal on said electrical signal conductor indicative of a pressure acting on said forward end;
    an elongate tip in said forward end for insertion in a periodontal pocket;
    measurement means mounted externally on said tip for simultaneously measuring periodontal pocket depth and periodontal tooth attachment level and for providing first and second depth signals to said electrical signal conductor indicative of said pocket depth and attachment level,
    a signal processing apparatus connected to said electrical signal conductor, which responds to pressure signals by receiving and converting first and second depth signals into measurement signals, which accumulates a file of measurement signals, and which stores an accumulated file of measurement signals in an examination file format; and
    a display appratus which responds to converted first and second depth signals by visibly displaying pocket depth and attachment level in a dental chart format.

2. The system of claim 1 further including a differential process modality in said signal processing apparatus which compares a first file of measurement signals with a second file of measurement signals and which produces a set of differential measurement signals representative of changes in pocket depth and attachment level based upon said comparison.

3. The system of claim 2 wherein said display apparatus further responds to said set of differential measurement signals by visibly displaying changes in pocket depth and attachment level in said dental chart format.

4. The system of claim 1 wherein said measurement means includes an array of opto-electrical elements disposed on said elongate tip and an optical shield slidably disposed on said tip over said array.

5. The system of claim 4 wherein said array includes an elongate strip of serially-connected CCD cells longitudinally disposed on said tip.

6. The system of claim 4 wherein said optical shield includes an annular collar encircling said tip, a crown engagement member radially attached to said collar, and a spring attached to and acting between said tip and said collar.

7. An apparatus for making periodontal measurements, comprising:
    a probe assembly with a probing portion having a forward end and a grasping portion;
    an elongate tip in said forward end of said probing portion for insertion in a periodontal pocket or gingival sulcus adjacent a tooth, said tip having an external measuring surface; and
    an opto-electronic sensor disposed on said external measuring surface which provides a plurality of light transition signals corresponding to changes in illumination which occur longitudinally along said tip.

8. The apparatus of claim 7 wherein said opto-electronic sensor includes:
    an elongate array of optically-activated elements disposed longitudinally on said tip; and
    an optical shield slidably disposed on said tip over said array of elements.

9. The apparatus of claim 8 wherein said shield includes an annular collar encircling said tip, and a crown-engagement member radially attached to said collar.

10. The apparatus of claim 9 wherein said shield further includes a spring apparatus connected to said tip and said collar, which returns said collar to a predetermined position.

11. The apparatus of claim 7 further including a pressure sensor means for indicating an amount of probing pressure applied to said tip while said measurements are made.

12. A method for making periodontal measurements with a periodontal probe apparatus that includes a probe, a tip in said probe, an illumination detector mounted externally on said tip, and a sensor which measures the force applied on said tip, comprising the steps of:
    illuminating the interior of a patient's mouth;

inserting said tip into a periodontal pocket or gingival sulcus adjacent a tooth in the illuminated mouth;

exerting a force on said tip via said probe while said tip is in said periodontal pocket or gingival sulcus; and when said force reaches a predetermined level,
  detecting illumination transitions along said tip; and
  converting said illumination transitions into respective pocket depth and attachment level measurements.

13. The method of claim 12 wherein said illumination detector includes an elongate array of optical detectors arranged longitudinally on said tip and an optical shield slidable on said tip over said elongate array, and wherein said step of inserting includes positioning said optical shield at the crown of said tooth and said step of detecting includes detecting illumination transitions on said array caused by said optical shield and by said periodontal pocket or gingival sulcus.

14. The method of claim 12 further including the step of providing a visible indication of pocket depth and attachment level in a dental chart format in response to said step of converting.

15. A periodontal measurement system, comprising:
a probe with an end and a handle surface;
means for indicating the magnitude of force applied between said end and said handle surface;
an elongate measurement tip in said end;
measurement means on an external surface of said tip for obtaining simultaneous optical indications of periodontal pocket depth and attachment level in a single measurement and for providing first and second depth signals indicative of said depth and said level;
means responsive to an indication of a predetermined force level for converting first and second depth signals into corresponding first and second measurement signals;
first processing means for accumulating a set of said first and second measurement signals resulting from a plurality of measurements;
second processing means for storing an accumulated set of measurement signals in a predetermined examination record format;
third processing means for providing a marker signal indicating a predetermined measuring sequence; and
display means for displaying converted first and second depth signals in a dental chart format while displaying said predetermined measuring sequence in said dental chart format in response to said marker signal.

16. A periodontal measurement tip for making measurements of periodontal pocket depth and periodontal attachment level, comprising:
an elongate member for insertion in a periodontal pocket, the member having an external measurement surface;
an opto-electronic sensor disposed on said external measuring surface for providing a plurality of light transition signals corresponding to changes in illumination which occur along said member; and
an optical shield slidably disposed on said member over said opto-electronic sensor, said shield causing a change of illumination on said member corresponding to an attachment level reference.

17. The periodontal measurement tip of claim 16, wherein said opto-electronic sensor includes an elongate array of optically sensitive elements disposed longitudinally on said member.

18. The periodontal measurement tip of claim 17 further including a keyed endpiece on an end of said member.

19. The periodontal measurement tip of claim 16, wherein said optical shield includes an annular collar encircling said member, and an engagement member radially attached to said collar.

20. The periodontal measurement tip of claim 19, wherein said optical shield further includes a spring apparatus acting between said member and said collar which returns said collar to a predetermined location.

* * * * *